United States Patent
Liang et al.

(10) Patent No.: US 8,207,122 B2
(45) Date of Patent: Jun. 26, 2012

(54) **ANTI-CANCER BIOACTIVE PEPTIDES ISOLATED FROM CRUDE VENOM OF XINJIANG *LYCOSA SINGORIENSIS***

(75) Inventors: Songping Liang, Xiamen (CN); Zhonghua Liu, Xiamen (CN)

(73) Assignee: Xiamen Bioway Biotech Co., Limited, Xiamen (CN)

( * ) Notice: Subject to any disclaimer, the term of this patent is extended or adjusted under 35 U.S.C. 154(b) by 130 days.

(21) Appl. No.: 12/697,320

(22) Filed: Feb. 1, 2010

(65) Prior Publication Data

US 2010/0145012 A1    Jun. 10, 2010

Related U.S. Application Data

(63) Continuation of application No. PCT/CN2008/071804, filed on Jul. 30, 2008.

(30) Foreign Application Priority Data

Jul. 31, 2007 (CN) .......................... 2007 1 0035478

(51) Int. Cl.
*A61P 35/00* (2006.01)
*C07K 14/435* (2006.01)

(52) U.S. Cl. .......................... 514/19.3; 530/300; 514/1.1

(58) Field of Classification Search .................. None
See application file for complete search history.

(56) References Cited

U.S. PATENT DOCUMENTS 5,756,462 A * 5/1998 Kelbaugh et al. ............ 514/21.3

* cited by examiner

*Primary Examiner* — Elly-Gerald Stoica
(74) *Attorney, Agent, or Firm* — Matthias Scholl P.C.; Scholl, Matthias

(57) ABSTRACT

An anti-cancer bioactive peptide having an amino acid sequence as shown in SEQ ID NO.1, or a functional analogue thereof prepared by substitution, insertion, or deletion of one or more amino acids of SEQ ID NO. 1, or a peptide having 90% homology in amino acid sequence with that of SEQ ID NO. 1. The anti-cancer bioactive peptide of the invention can selectively kill cancer cells and exhibit low cytotoxicity against normal cells.

3 Claims, 3 Drawing Sheets

SEQUENCE LISTING

<160> NUMBER OF SEQ ID NOS: 5

<210> SEQ ID NO 1
<211> LENGTH: 24
<212> TYPE: PRT

<213> ORGANISM: Lycosa singoriensis
<220> FEATURE:
<221> NAME/KEY: MOD_RES
<222> LOCATION: (24)..(24)
<223> OTHER INFORMATION: AMIDATION

<400> SEQUENCE: 1

Arg Lys Gly Trp Phe Lys Ala Met Lys Ser Ile Ala Lys Phe Ile Ala
1               5                   10                  15

Lys Glu Lys Leu Lys Glu His Leu
            20

<210> SEQ ID NO 2
<211> LENGTH: 23
<212> TYPE: PRT
<213> ORGANISM: Lycosa singoriensis
<220> FEATURE:
<221> NAME/KEY: MOD_RES
<222> LOCATION: (23)..(23)
<223> OTHER INFORMATION: AMIDATION

<400> SEQUENCE: 2

Lys Gly Trp Phe Lys Ala Met Lys Ser Ile Ala Lys Phe Ile Ala Lys
1               5                   10                  15

Glu Lys Met Lys Glu His Leu
            20

<210> SEQ ID NO 3
<211> LENGTH: 23
<212> TYPE: PRT
<213> ORGANISM: Artificial Sequence
<220> FEATURE:
<223> OTHER INFORMATION: Fully synthetic peptide
<220> FEATURE:
<221> NAME/KEY: MOD_RES
<222> LOCATION: (23)..(23)
<223> OTHER INFORMATION: AMIDATION

<400> SEQUENCE: 3

Lys Gly Trp Phe Lys Ala Met Lys Ser Ile Ala Lys Phe Ile Ala Lys
1               5                   10                  15

Glu Lys Leu Lys Glu His Leu
            20

<210> SEQ ID NO 4
<211> LENGTH: 18
<212> TYPE: PRT
<213> ORGANISM: Artificial Sequence
<220> FEATURE:
<223> OTHER INFORMATION: Fully synthetic peptide

<400> SEQUENCE: 4

Trp Phe Lys Ala Met Lys Ser Ile Ala Lys Phe Ile Ala Lys Glu Lys
1               5                   10                  15

Leu Lys

<210> SEQ ID NO 5
<211> LENGTH: 12
<212> TYPE: PRT
<213> ORGANISM: Artificial Sequence
<220> FEATURE:
<223> OTHER INFORMATION: Fully synthetic peptide
<220> FEATURE:
<221> NAME/KEY: MOD_RES
<222> LOCATION: (12)..(12)
<223> OTHER INFORMATION: AMIDATION

```
<400> SEQUENCE: 5

Lys Ala Met Lys Ser Ile Ala Lys Phe Ile Ala Lys
1               5                   10
```

ANTI-CANCER BIOACTIVE PEPTIDES ISOLATED FROM CRUDE VENOM OF XINJIANG *LYCOSA SINGORIENSIS*

CROSS-REFERENCE TO RELATED APPLICATIONS

This application is a continuation of International Patent Application No. PCT/CN2008/071804 with an international filing date of Jul. 30, 2008, designating the United States, now pending, and further claims priority benefits to Chinese Patent Application No. 200710035478.8 filed Jul. 31, 2007. The contents of all of the aforementioned applications, including any intervening amendments thereto, are incorporated herein by reference

BACKGROUND OF THE INVENTION

1. Field of the Invention

The invention relates to an anti-cancer bioactive peptide, and more particularly to an anti-cancer bioactive peptide isolated from crude venom of Xinjiang *Lycosa singoriensis*.

2. Description of the Related Art

Anti-cancer bioactive peptides have aroused more and more attention in recent years. However, most of conventional anti-cancer bioactive peptides have low bioactivity and strong toxicity, those suitable for clinical use as anti-cancer active ingredient is seriously insufficient. Therefore, it is very urgent to develop an anti-cancer bioactive peptide having high bioactivity and low toxicity.

SUMMARY OF THE INVENTION

In view of the above-described problems, it is one objective of the invention to provide an anti-cancer bioactive peptide having high bioactivity and low toxicity.

To achieve the above objectives, in accordance with one embodiment of the invention, there is provided an anti-cancer bioactive peptide having high bioactivity and low toxicity, the anti-cancer bioactive peptide comprising an amino acid sequence of SEQ ID NO. 1,

```
SEQ ID NO. 1:
Arg Lys Gly Trp Phe Lys Ala Met Lys Ser Ile Ala
 1               5                  10

Lys Phe Ile Ala Lys Glu Lys Leu Lys Glu His Leu-
            15                  20

NH₂ (the C-terminal is amidated).
```

The anti-cancer bioactive peptide has 24 amino acids and is isolated and purified from crude venom of Xinjiang *Lycosa singoriensis*. Optionally, the peptide can be synthesized artificially by a chemical process. It can induce apoptosis, inhibit the proliferation of or even kill a variety of cancer cells, but exhibits weak toxicity on normal cells and animals. Additionally, the peptide can effectively inhibit the growth of solid tumor by inhibiting the transcriptional activity of hypoxia-inducible factor (HIF-α) and inhibiting tumor angiogenesis. Its anti-cancer activity has high efficiency and low toxicity, which brings a good prospect for developing anti-cancer drugs of solid tumors such as lung cancer, liver cancer, and cervical cancer. Since the peptide can optionally be synthesized in large scale by a chemical process, the development cost is low, and the production rate thereof is high.

In a class of this embodiment, one or more amino acids of the peptide of SEQ ID NO. 1 are substituted, inserted, or deleted and the resultant peptide still has the anti-cancer bioactivity.

In a class of this embodiment, the peptide having high anti-cancer activity and low toxicity comprises a peptide which has 90% homology in amino acid sequence with SEQ ID NO. 1.

In a class of this embodiment, the peptide has an amino acid sequence of

```
SEQ ID NO. 2:
Lys Gly Trp Phe Lys Ala Met Lys Ser Ile Ala Lys

Phe Ile Ala Lys Glu Lys Met Lys Glu His Leu-NH₂.
```

In a class of this embodiment, the peptide has an amino acid sequence of

```
SEQ ID NO. 3:
Lys Gly Trp Phe Lys Ala Met Lys Ser Ile Ala Lys

Phe Ile Ala Lys Glu Lys Leu Lys Glu His Leu-NH₂.
```

In a class of this embodiment, the peptide has an amino acid sequence of

```
SEQ ID NO. 4:
Trp Phe Lys Ala Met Lys Ser Ile Ala Lys Phe Ile

Ala Lys Glu Lys Leu Lys.
```

In a class of this embodiment, the peptide has an amino acid sequence of

```
SEQ ID NO. 5:
Lys Ala Met Lys Ser Ile Ala Lys Phe Ile Ala Lys-

NH₂.
```

SEQ ID NO. 2 is isolated from crude venom of Xinjiang *Lycosa singoriensis*. It is an analogue of SEQ ID NO. 1 except that SEQ ID NO. 2 has no Arg at the N-terminal and the 19th position is Met but not Leu. However, the two sequences have the same activity.

After studying the molecular structure and anti-cancer activity of SEQ ID NO. 1, SEQ ID NOS. 3-5 as variants are synthesized. SEQ ID NOS. 3 and 4 have the same activity as that of SEQ ID NO. 1, while the activity of SEQ ID NO. 5 has been increased by about 10 times. All the sequences have strong hemolytic activity, which is the same as that of SEQ ID NO. 1.

BRIEF DESCRIPTION OF THE DRAWINGS

The invention is described hereinbelow with reference to accompanying drawings, in which:

FIGS. 5-8 show a peptide effectively inhibits the growth of tumors, wherein

FIG. 5 is a monitoring map of volume change of tumor according to one embodiment of the invention, wherein ○ refers to a sample group, ○ refers to a control group; the result shows the growth of the tumor in the control group continues, while that in the sample group is inhibited;

FIG. 6: the left map shows the tumor volume before administration and after the last administration, which is a mean value of all nude mice from the control group and from the sample group respectively, the black column refers to "before administration", the grey column refers to "after administration"; the right map shows the tumor weight of all nude mice from the control group and from the sample group respectively, the mean weight of tumors of the control group is 5 times that of the sample group;

FIG. 7 is a comparative map of inhibition of five kinds of peptide (SEQ ID NOS. 1-5) on the growth of Hela cells according to one embodiment of the invention; and FIG. 8 is a comparative map of hemolytic activity between SEQ ID NO.1 and SEQ ID NO.5 according to one embodiment of the invention.

DETAILED DESCRIPTION OF THE EMBODIMENTS

Figure 1:
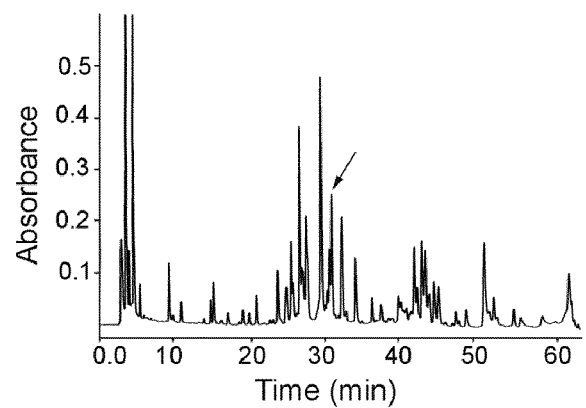
FIG. 1 is an isolation and purification map of crude venom of *Lycosa singoriensis* by RP-HPLC according to one embodiment of the invention.

For further illustrating the invention, experiments detailing an anti-cancer bioactive peptide and the bioactivity thereof are described below. It should be noted that the following examples are intended to describe and not to limit the invention.

A peptide having anti-cancer activity is isolated and purified from crude venom of Xinjiang *Lycosa singoriensis* by highly sensitive analytical RP-HPLC, and the amino acid sequence thereof is determined by Edman degradation technology. The result shows the amino acid sequence has a very low similarity with that of the existing anti-cancer bioactive peptides. Thus, it is a novel molecule.

Isolation and purification of the peptide from crude venom of Xinjiang *Lycosa singoriensis*

A dry powder of crude venom of Xinjiang *Lycosa singoriensis* was dissolved with double-distilled water to yield a solution (5 mg/mL). The solution was centrifuged at 8,000 rpm for 5 min, and the resultant supernatant was filtered with a disposable filter (0.22 mmol, manufactured by Millipore Corporation) and stored at 4° C. The crude venom was directly isolated by analytical RP-HPLC (Vydac, C18, 218TP54, 4.6×250 mm), a sample volume was 0.5 mg, the eluents were 0.1% trifluoroacetic acid/water and 0.1% trifluoroacetic acid/acetonitrile (Solution B) respectively, elution gradient: 0-60 min, 0-60% Solution B, 1 mL/min, 40° C. The peak component was collected at a wavelength of 215 nm, the molecular weight measured with a matrix-assisted dissociation time of flight mass spectrometer, and freeze dried to yield a dry power of anti-cancer peptide.

Chemical Synthesis of the Peptide

The peptide was synthesized by a solid phase peptide synthesis method with fluorenylmethoxycarbonyl (FMOC)-amino acid as raw materials and TBTu/HOBt as a coupling agent. A solid phase carrier was Rink resin. An automatic synthesizer PS3 (PTI) was used. The addition amount of FMOC-amino acid was fivefold excess (0.5 mm). The coupling time for each amino acid residue was 30 min. Terminal FMOC was removed with 20% piperidine/dimethyl formamide (volume ratio). Finally, the peptide resin was washed with methanol completely and freeze dried. The freeze-dried peptide resin was put into a BIO-RAD reaction column having sieve plates, a cracking agent K (Formula:trifluoroacetic acid:water:phenol:methyl phenyl sulfide:dimercaptoethane=82.5:5:5:5:2.5 (volume ratio)) added, 2 hours later, side-chain protecting groups were removed and the peptide was separated from the resin. The peptide was precipitated with cold ether, washed several times, and dried under freezing and vacuum conditions to yield a crude peptide. The crude peptide was isolated by a semi-preparative RP-HPLC (reversed phase column: 10×250 mm Elite C18; linear gradient Solution B 15-45%, 30 min; flow rate of 3 mL/min), and an elution peak was collected and freeze dried for further use.

To verify whether the peptide (isolated from crude venom of Xinjiang *Lycosa singoriensis* or synthesized artificially) had anti-cancer activity, cytotoxicity experiments were carried out by MTT assay, and to verify the inhibitory activity on the growth of solid tumor, experiments on tumor-bearing nude mice were carried out.

1. Equipment and Materials

*Lycosa singoriensis* was collected from Hami, Xinjiang province, and bred at Protein Chemistry Laboratory, the College of Life Sciences, Hunan Normal University. Crude venom was obtained by electrical stimulation, freeze dried, and stored at −20° C. Nude mice were purchased from Shanghai. All sequencing reagents were purchased from American Applied Biosystems Corporation. Solid-phase chemical synthesis reagents were purchased from Chemassist Ltd. MTT (3-(4,5-dimethyl-2-thiazolyl)-2,5-diphenyl tetrazolium bromide) and fluorescein isothiocyanate were purchased from Sigma Corporation. Annexin V-fluorescein isothiocyanate/propidium iodide double staining kit was purchased from Nanjing KeyGen Biotech Co., Ltd. Fetal calf serum was purchased from Sijiqing Co., Ltd. DMEM and RPMI 1640 as culture medium were purchased from Gibico Co., Ltd. Other reagents were analytical grade reagents produced in China.

Cell strains: Hela, HT1080, JB6, and HNE1.

Equipment: Matrix-assisted laser desorption ionization time of flight mass spectrometer, 491A Gas phase sequencer, Fluorescence microscope, Fluorescence spectrophotometer, Flow cytometer.

2. Experimental Results and Analysis Thereof 2.1 Crude Venom and Biological Characteristics Thereof Crude venom of *Lycosa singoriensis* was collected and purified by analytical RP-HPLC (as shown in FIG. 1). The marked peak was a single molecular weight peak by mass spectrometry identification, with monoisotopic molecular weight (M+H$^+$) of 2886.754 Da. Edman degradation showed primary structure of the peptide had 24 amino acid residues, without cysteine residue. Determination of molecular weight by comparative experiment and theoretical calculation showed the C-terminal of the peptide was amidated. Sequence analysis revealed that the peptide had a typical feature, i.e., contained seven lysine residues, with theoretical pI of about 10.78, and Lys was distributed regularly in the $KX_nK$ (X represents hydrophobic amino acid residues) model of the whole amino acid sequence. Circular dichroism showed that the peptides could form α-helical conformation. By drawing helical wheel of the peptide, it showed clearly that the polar amino acid residues were distributed at the α-helix side, while hydrophobic amino acid residues were distributed at the opposite side. Thus, it was an amphipathic α-helix.

2.2 The Synthesized Peptide and Biological Characteristics Thereof

Figure 2:
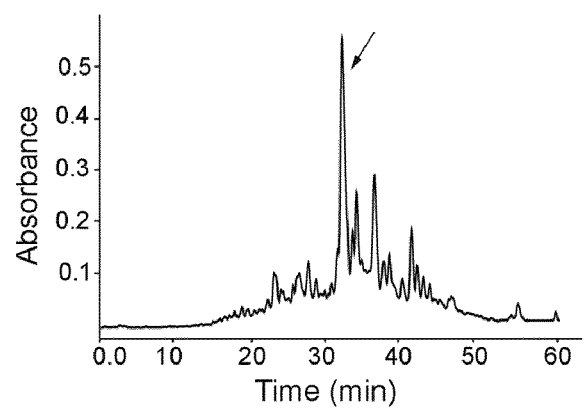
FIG. 2 is an isolation and purification map of a chemically-synthesized anti-cancer peptide by RP-HPLC according to one embodiment of the invention, wherein the arrow refers to the target peak.

In *Lycosa singoriensis*, the crude venom content was low, and thereby the isolated peptide was very small. However, a large amount of products can be prepared by chemical synthesis. Consisting of merely 24 amino acid residues, the peptide can be synthesized easily. The peptide was synthesized in a scale of 0.1 mm, and proved to have high purity by MS identification, with monoisotopic molecular weight (M+H$^+$) of 2886.621 Da (as shown in FIG. 2), which was the same as that of the natural peptide isolated from Xinjiang *Lycosa singoriensis*.

2.3 The Selective Killing of the Peptide on Cancer Cells

Figure 3:
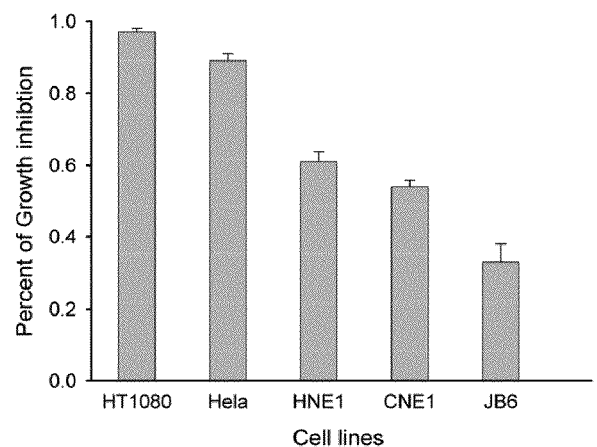
FIG. 3 is a cytotoxicity map of a peptide by MTT method according to one embodiment of the invention, which shows 40 μmol of the peptide has obvious killing effect on the five kinds of cell strains.

The cytotoxicity of the peptide on cell strains such as Hela, HT1080, HNE1, CNE1, and JB6 were assayed by MTT. 40 μmol of the peptide had obvious killing capacity on the above mentioned cell strains (as shown in FIG. 3), among which the killing capacity against HT1080 and Hela was the strongest, against JB6 was the weakest, with a killing rate of 98% and 36% respectively. Thus, the peptide had different sensitivity on different cancer cells. HT1080 and Hela were cell strains of fibrosarcoma and cervical cancer respectively. JB6 was cell strain of immortalized mouse epithelial cell, it could be subcultured, but without malignant proliferation. These results showed that the peptide killed cancer cells selectively.

To examine the cytotoxicity of the peptide on normal cells, hemolytic test was carried out. The results showed 200 μmol of the peptide could only cause 20% red cells cracked, which meant the peptide had weak cytotoxicity on normal cells. The cytotoxicity of the peptide was also studied on a whole animal, that is, 200 mg/Kg (body weight) of the peptide was administered to mice by subcutaneous injection, while no obvious toxic reaction was observed within 48 hours. Thus, the peptide had low cytotoxicity on normal cells, and had high selectivity on cancer cells.

Figure 4:
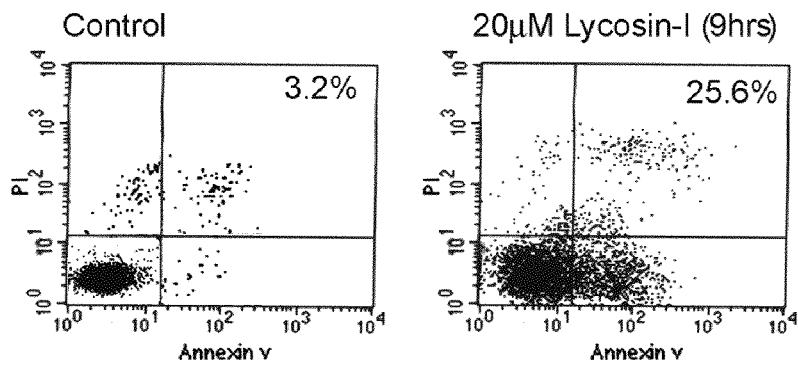
FIG. 4 is an apoptosis map of peptide-reduced Hela cells detected by fluorescein isothiocyanate-Annexin V/propidium iodide double staining method according to one embodiment of the invention; it is a scatter diagram of bivariate flow cytometry, at the lower right quadrant are early apoptotic cells.

The kill mechanism of the peptide on cancer cells was studied by Annexin V-fluorescein isothiocyanate/propidium iodide double staining method. The results showed the peptide induced apoptosis of Hela cells, as shown in FIG. 4. 20 μmol of the peptide could cause apoptosis of 25.6% Hela cells, while the apoptosis rate of those untreated with the peptide was low, which showed the peptide killed cancer cells by inducing apoptosis thereof.

2.4 The Peptide Inhibits the Growth of Tumor-Bearing Nude Mice

Figure 5:
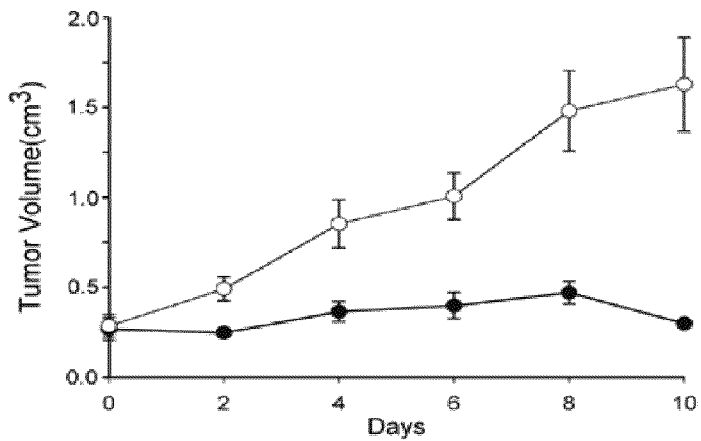
Figure 6:
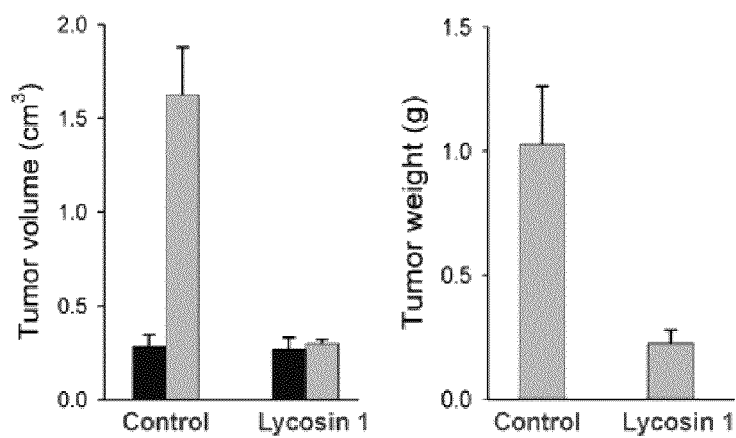

Although the above-mentioned experiments have proved the peptide has high efficiency in inhibiting the growth of cancer cells, further experiments are still required to prove the inhibitory activity in vivo. A tumor-bearing nude mice model was established. The results showed the peptide of the invention could obviously inhibit the growth of solid tumors. As shown in FIG. 5, prior to administration of the peptide (i.e., 0 day), the volume of the solid tumor of the control group and the sample group was basically equal. Subsequently, the control group was administered with normal saline, and the tumor volume thereof increased quickly, which meant the tumor grew continuously. The sample group was administered with the peptide, and the tumor volume thereof almost had no change, even in one nude mouse the tumor vanished completely after the 3th administration, which meant the growth of tumor was inhibited. At the 10th day after administration, the tumor volume of the control group was 5 times that of the sample group (P<0.05) (as shown in FIG. 6). The nude mice were killed and the solid tumor collected. Obviously, the tumor from the sample group was much smaller than that from the control group, and the weight of the control group was 5 times that of the sample group (P<0.03) (as shown in FIG. 6). All these showed the peptide could effectively inhibit the growth of tumor.

To study the inhibition mechanism of the peptide on cancer cells and solid tumors, the tumor sections were stained with hematoxylin and eosin. The results showed, the tumor cells in the control group arranged tightly and regularly, the cell nucleus was stained light blue, while those in the sample group arranged loosely, the cell nucleus was concentrated and stained dark blue. All these showed the peptide inhibited the growth of tumor cells by inducing apoptosis thereof.

2.5 Comparison of Inhibitory Activity of Peptides on Hela Cells

The above-mentioned experiments have verified the peptide has strong inhibition on the growth of cancer cells and solid tumors. In order to study the inhibition degree of difference sequences (SEQ. Nos. 1-5) of the peptide on tumor cells, comparative experiments of measuring the activity of Hela cells were conducted (as shown in FIG. 7).

Figure 7:
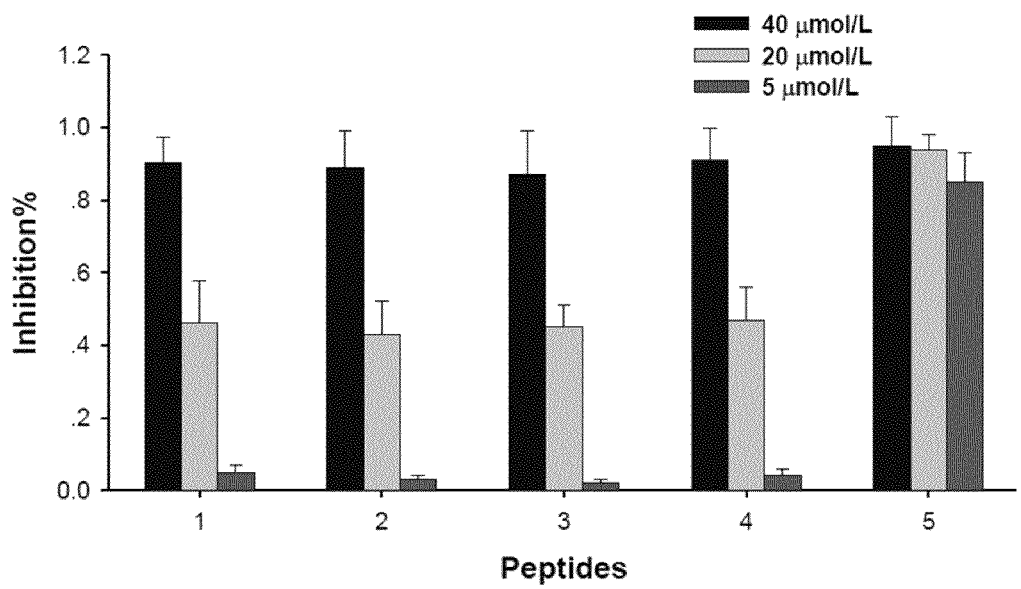
Figure 8:
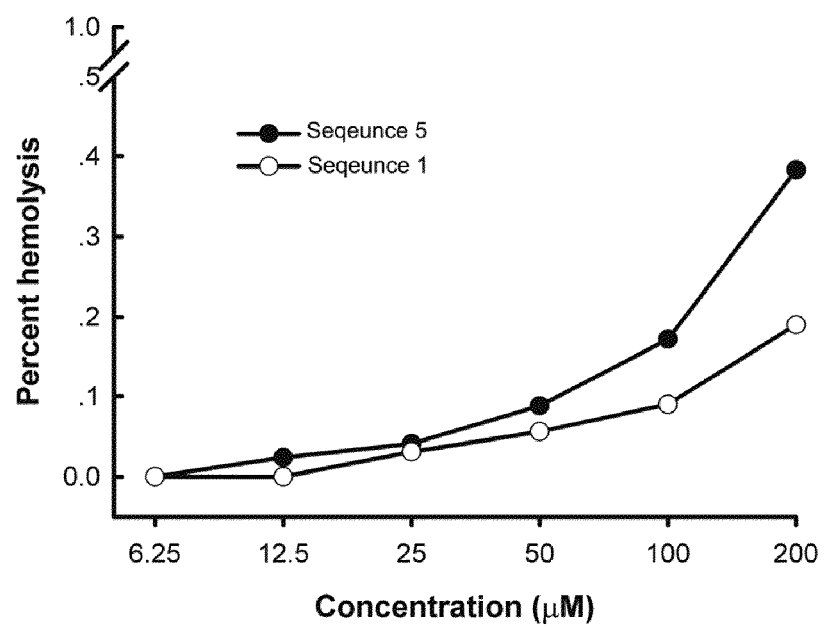

As shown in FIG. 7, for SEQ. Nos. 1-4, at a concentration of 40 μmol/L, the inhibition rate on Hela cells was about 90%, at 20 μmol/L, about 50%, at 5 μmol/L, only 2%. Thus, the inhibition degree of SEQ. Nos. 1-4 on Hela cells was basically equal. However, for SEQ. No. 5, at a concentration of 40 μmol/L, 20 μmol/L, and 5 μmol/L, the inhibition rate on Hela cells was more than 80%. Compared with that of SEQ. Nos. 1-4, the inhibition degree of SEQ. No. 5 had been increased by about 10 times. As shown in FIG. 8, at 200 μmol, SEQ. No. 1 and SEQ. No. 5 could dissolve 19% and 37% red cells respectively, which meant the hemolytic activity of SEQ. No. 5 was better than that of SEQ. No. 1.

Industrial Applicability

The anti-cancer peptide having high bioactivity and low toxicity can be isolated and purified from natural venom or synthesized in a large scale by a chemical process. A large number of pharmacological studies have shown that the peptide of this invention has a good prospect for development of anti-cancer pharmaceutical compositions, these cancers including but not limited to lung cancer, liver cancer, and cervical cancer.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

---

The invention claimed is:

1. An isolated anti-cancer bioactive peptide having an amino acid sequence as shown in SEQ ID NO:2.

2. An isolated anti-cancer bioactive peptide having an amino acid sequence as shown in SEQ ID NO:3.

3. An isolated anti-cancer bioactive peptide consisting of the amino acid sequence as shown in SEQ ID NO:1, SEQ ID NO:2, SEQ ID NO:3, or SEQ ID NO:4.

* * * * *